United States Patent
Wang et al.

(10) Patent No.: US 10,781,467 B2
(45) Date of Patent: Sep. 22, 2020

(54) 3-EPIMERASE AND POLYNUCLEOTIDE ENCODING SAME

(71) Applicants: Langnai Biotech Co., LTD, Nanjing (CN); L&P Food ingredient Co. LTD, Shaoguan (CN)

(72) Inventors: Sanyong Wang, Shaoguan (CN); Chunrong Li, Shaoguan (CN); Shilei Han, Shaoguan (CN); Ming Yan, Nanjing (CN); Miao Wei, Nanjing (CN); Sheng Chen, Nanjing (CN); Zhilin Zhang, Nanjing (CN)

(73) Assignees: LANGNAI BIOTECH CO., LTD, Nanjing (CN); L&P FOOD INGREDIENT CO., LTD, Shaoguan (CN)

( * ) Notice: Subject to any disclaimer, the term of this patent is extended or adjusted under 35 U.S.C. 154(b) by 0 days.

(21) Appl. No.: 16/088,821

(22) PCT Filed: Mar. 31, 2017

(86) PCT No.: PCT/CN2017/078923
§ 371 (c)(1),
(2) Date: Sep. 27, 2018

(87) PCT Pub. No.: WO2017/167255
PCT Pub. Date: Oct. 5, 2017

(65) Prior Publication Data
US 2019/0136282 A1 May 9, 2019

(30) Foreign Application Priority Data

Apr. 1, 2016 (CN) .......................... 2016 1 0047300

(51) Int. Cl.
*C12N 9/90* (2006.01)
*C12P 19/02* (2006.01)
(Continued)

(52) U.S. Cl.
CPC .............. *C12P 19/24* (2013.01); *A23L 27/33* (2016.08); *C12N 9/90* (2013.01); *C12N 15/52* (2013.01);
(Continued)

(58) Field of Classification Search
None
See application file for complete search history.

(56) References Cited

U.S. PATENT DOCUMENTS 10,480,018 B2 * 11/2019 Venkitasubramanian .................. C12P 19/24

FOREIGN PATENT DOCUMENTS

| CN | 101189332 | 5/2008 |
| CN | 103131721 | 6/2013 |

(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Treasure IP Group, LLC

(57) ABSTRACT

Provided are a 3-epimerase, an encoding polynucleotide therefor, a nucleic acid construct, vector, and host cell comprising the polynucleotide, a method for producing the 3-epimerase, and use of the 3-epimerase.

8 Claims, 3 Drawing Sheets

Specification includes a Sequence Listing.

(51) Int. Cl.
*C12P 19/24* (2006.01)
*A23L 27/30* (2016.01)
*C12N 15/52* (2006.01)

(52) U.S. Cl.
CPC ....... *C12P 19/02* (2013.01); *C12Y 501/03001* (2013.01); *C12Y 501/03022* (2013.01)

(56) References Cited

FOREIGN PATENT DOCUMENTS

| | | |
|---|---|---|
| CN | 104160023 | 11/2014 |
| CN | 105821027 | 8/2016 |
| EP | 2944691 A1 | 11/2015 |

OTHER PUBLICATIONS

GenBanK, "Registry No. WP_052889376", GenBanK Database, Aug. 20, 2015 1-3 (Aug. 20, 2015), see the amino acid sequence.
GenBank, "Registry No. WP_052889376", GenBanK Database, Aug. 20, 2015 4-13 (Aug. 20, 2015), see the amino acid sequence.
Emboss: The European Molecular Biology Open Software Suite, Rice ?, 2000, Trends in Genetics 16: 276-277 Needleman and Wunsch, 1970, J. Mol. Biol. 48: 443-453.
Longtao Zhang et al: "Characterization of d-tagatose-3-epimerase from Rhodobacter sphaeroides that converts d-fructose into d-psicose", Biotechnology Letters, Springer Netherlands, Dordrecht, vol. 31, No. 6, Feb. 11, 2009 (Feb. 11, 2009), pp. 857-862, XP019670323, ISSN: 1573-6776.

* cited by examiner

3-EPIMERASE AND POLYNUCLEOTIDE ENCODING SAME

CROSS REFERENCE TO RELATED APPLICATION

This application claims priority to a PCT application PCT/CN2017/078923, filed on Mar. 31, 2017, which in turn takes priority of Chinese Application No. 201610047300.4, filed on Apr. 1, 2016. Both the PCT application and Chinese Application are incorporated herein by reference in their entireties.

BACKGROUND

Technical Field

The present invention relates to a polypeptide or protein having 3-epimerase activity, a polynucleotide sequence encoding the polypeptide or protein having 3-epimerase activity, a nucleic acid construct or expression vector comprising the polynucleotide sequence, a method for producing the enzyme, and use of the enzyme in a variety of industrial applications.

Further, the present invention relates to a method for catalytically producing D-allulose with a single sugar such as fructose, glucose and starch, or a mixture thereof, by using a polypeptide or protein having 3-epimerase activity, and a method for catalytically producing D-tagatose with a single sugar such as sorbose and starch, or a mixture thereof, by using the polypeptide or protein.

Related Art

With the increasing emphasis on healthy eating, the development of healthy and safe low-calorie functional sweeteners has become a focus of research in the food industry. D-allulose and D-tagatose, as natural low-calorie functional sweeteners that are naturally occurring, but lowly present in nature, have become research hotspots.

D-allulose, also known as D-ribo-2-hexulose, is an epimer of D-fructose isomerized at the C-3 position. D-allulose is a naturally occurring, but lowly present low-calorie functional sweetener with a sweetness that is 70% of the sweetness of sucrose, but with an caloric energy that is only 0.3% of the energy of sucrose, and can be used as a sweetener in low-calorie diet foods. Moreover, D-allulose also has the function of inhibiting the activity of enzymes involved in the lipid synthesis in the liver, contributes to the reduction of abdominal fat accumulation, and controls the body weight to some extent, thus being useful in various functional foods such as health food. In addition, D-allulose can also improve the flavor, appearance, etc. of food, and extend the shelf life of food. Therefore, D-allulose, a healthy and safe low-calorie functional sweetener, has attracted more and more attention and become one of the most competitive novel sweeteners.

D-allulose is a rare natural monosaccharide, and there are disadvantages such as low yield and high cost when it is separated and extracted from natural resources. Therefore, it is difficult to meet the demand for D-allulose since it is a low-calorie healthy sweeteners for which there currently is not a suitable method for industrialized large-scale production. As such, in order to be applicable to the food industry, an efficient method for producing D-allulose is needed. The traditional method for producing D-allulose is mainly a chemical method, which suffers from the disadvantages of high cost and production of many by-products and pollutants. Preparation of D-allulose by a biological method has the characteristics of high reaction specificity, simple product composition, convenient purification, and natural products, thus becoming a research hotspot.

The most effective way to prepare D-allulose by biological methods is to find an enzyme that converts fructose into D-allulose. However, the existing allulose-3-epimerase has problems such as reduced stability at high temperature or low activity and low reaction rate, which is not conducive to the cost control in industrial production of D-allulose. Therefore, there is a need to develop an allulose-3-epimerase with good high-temperature stability and high activity, to meet the needs in industrial production.

D-tagatose is an epimer of D-sorbose isomerized at the C-3 position. D-tagatose is a naturally occurring, but lowly present low-calorie functional sweetener with a sweetness that is 92% of the sweetness of sucrose, but with an low absorption rate of only 20 to 25% in humans, thus causing no obvious changes in blood glucose level in the body. Therefore, D-tagatose is suitable for consumption by patients with diabetes. Moreover, most of the tagatose will directly enter the colon, and be selectively fermented by the microbial flora therein, to promote the proliferation of beneficial bacteria, inhibit the growth of harmful bacteria, and significantly improve the intestinal flora. Therefore, D-tagatose is a good probiotic and can be used in a variety of functional foods such as health foods. In addition, D-tagatose can also improve the flavor, appearance, etc. of food. Therefore, D-tagatose, a healthy and safe low-calorie functional sweetener, has attracted more and more attention and become one of the most promising novel sweeteners.

Isomerization of sorbose to D-tagatose is one of the most effective methods for the preparation of D-tagatose by biological methods. The key to this method is to find an enzyme that converts sorbose into D-tagatose. The existing tagatose-3-epimerase has problems such as reduced stability at high temperature or low activity and low reaction rate, which is not conducive to the cost control and scale up in industrial production of D-tagatose. Therefore, there is a need to develop a tagatose-3-epimerase having high-temperature stability and high activity to meet the needs in industrial production.

SUMMARY OF THE INVENTION

The present inventors have discovered a novel protein having 3-epimerase activity from the *Thermogemmatispora carboxidivorans*. Correspondingly, the present invention provides a novel protein having 3-epimerase activity, and a polynucleotide encoding the protein or polypeptide. The protein or polypeptide has allulose-3-epimerase and tagatose-3-epimerase activity. The protein or polypeptide of the present invention has good activity and excellent thermal stability, both of which are excellent properties for producing D-allulose and D-tagatose under high temperature conditions.

The present invention relates to an isolated protein or polypeptide having allulose-3-epimerase and tagatose-3-epimerase activity, which is selected from the group consisting of:

(a) a protein or polypeptide, having at least 70% sequence identity to the amino acid sequence as shown in SEQ ID No: 2;

(b) a protein or polypeptide, encoded by a polynucleotide hybridized, under conditions from moderate stringent to high sctringent, to (i) a sequence encoding a polypeptide as shown in SEQ ID No: 1, (ii) a genomic DNA sequence comprising the sequence encoding a polypeptide as shown in SEQ ID No: 1, or (iii) a full-length complement strand of (i) or (ii);

(c) a protein or polypeptide, encoded by a polynucleotide having at least 70% sequence identity to the sequence encoding a protein or polypeptide as shown in SEQ ID No: 1;

(d) a variant of the protein or polypeptide as shown in SEQ ID No: 2, comprising one or more (several) amino acid substitutions, deletions and/or insertions; and (e) any protein or polypeptide of (a), (b) or (c), having an amino acid sequence comprising or consisting of the sequence as shown in SEQ ID No: 2; and (f) a fragment of the protein or polypeptide of (a), (b), (c), (d), or (e), having the allulose-3-epimerase and tagatose-3-epimerase activity.

The present invention also relates to a nucleic acid construct, expression vector, and recombinant host cell comprising the polynucleotide, and to a method for producing the polynucleotide.

The present invention relates to a method for enzymatically producing D-allulose and D-tagatose.

Definitions

Allulose-3-epimerase activity: The term "allulose-3-epimerase activity" means the activity to catalyze the isomerization of fructose at the C-3 position into D-allulose.

Tagatose-3-epimerase activity: The term "tagatose-3-epimerase activity" means the activity to catalyze the isomerization of sorbose at the C-3 position into D-tagatose.

Isolated protein or polypeptide: The term "isolated protein or polypeptide" means a polypeptide that is isolated or purified relative to a protein or polypeptide found in nature. In an aspect, the polypeptide is at least 1% pure, for example at least 5% pure, at least 10% pure, at least 20% pure, at least 40% pure, at least 60% pure, at least 80% pure, and most preferably at least 90% pure, as determined by SDS-PAGE.

Non-limiting examples of isolated protein or polypeptide include (1) any non-naturally occurring protein or polypeptide, (2) any protein or polypeptide, including, but not limited to, any enzyme, variant, nucleic acid, protein, peptide or cofactor, which is at least partially removed from one or more or all naturally occurring components associated therewith in nature; (3) any protein or polypeptide that has been artificially modified relative to a protein or polypeptide found in nature; or (4) any protein or polypeptide that is modified in terms of increasing the amount of the protein or polypeptide over other components naturally associated therewith. The isolated protein or polypeptide may be present in a fermentation liquor sample.

Substantially pure protein or polypeptide: The term "substantially pure protein or polypeptide" means a protein or polypeptide preparation containing at most 10% by weight of other protein or polypeptide materials naturally or recombinantly associated therewith. Preferably, the protein or polypeptide is at least 90% pure by weight of all protein or polypeptide materials present in the preparation. The protein or polypeptide of the present invention is preferably in a substantially pure form, for example, this can be achieved by preparing the polypeptide by a well-known recombination method or by a typical purification method.

Sequence identity: The term "sequence identity" describes the correlation between two amino acid sequences or between two nucleotide sequences.

For the purpose of the present invention, the sequence identity between two amino acid sequences is determined by, for example, the Needleman-Wunsch algorithm (Needleman and Wunsch, 1970, J. Mol. Biol. 48: 443-453) executed by the Needle program in the EMBOSS software package (EMBOSS: The European Molecular Biology Open Software Suite, Rice et al, 2000, Trends in Genetics 16: 276-277) (preferably Version 3.0.0 or higher). The optional parameters used are a gap open penalty of 10, a gap extension penalty of 0.5 and an EBLOSUM62 (EMBOSS version of BLOSUM62) substitution matrix. The output result labeled as "longest identity" (obtained by using the nobrief option) by Needle is used as the percent identity and calculated as follows:

(the same residues×100)/(alignment length−the total number of gaps)

For the purpose of the present invention, the sequence identity between two nucleotide sequences is determined by, for example, the Needleman-Wunsch algorithm (Needleman and Wunsch, 1970, supra) executed by the Needle program in the EMBOSS software package (EMBOSS: The European Molecular Bi010 Open Software Suite, Rice et al., supra). The optional parameters used are a gap open penalty of 10, a gap extension penalty of 0.5 and EDNAFULL (EMBOSS version of NCBI NUC4. 4) substitution matrix. The output result labeled "longest identity" (obtained by using the nobrief option) by Needle is used as the percent identity and calculated as follows:

(the same deoxyribonucleotides×100)/(alignment length−the total number of gaps)

Fragment: The term "fragment" means a polypeptide having one or more (several) amino acids deleted from the amino and/or carboxyl terminus of a mature polypeptide, where the fragment has 3-epimerase activity.

Allelic variant: The term "allelic variant" means any two or more alternative forms of a gene occupying the same chromosomal locus. Allelic variation occurs naturally by mutation and can result in polymorphism within the population. The genetic mutation may be silent (no change in the encoded polypeptide) or may encode a polypeptide with an altered amino acid sequence. An allelic variant of a polypeptide is a polypeptide encoded by an allelic variant of a gene.

Isolated polynucleotide: The term "isolated polynucleotide" means a polynucleotide that is modified or purified by concentration of desired material relative to a polynucleotide found in nature. In one aspect, the isolated polynucleotide is 1 to 95% pure as determined by agarose electrophoresis. The polynucleotide may be of genomic, cDNA, RNA, semi-synthetic or synthetic origin, or any combination thereof.

Substantially pure polynucleotide: The term "substantially pure polynucleotide" means a polynucleotide preparation free of other extraneous or undesired nucleotides, which is in a form suitable for use in a genetically engineered protein production system. Thus, a substantially pure polynucleotide contains from 0.5% to 10% by weight of other polynucleotide materials naturally or recombinantly associated therewith. However, a substantially pure polynucleotide may include naturally occurring 5' and 3' untranslated regions, such as promoters and terminators. Preferably, a substantially pure polynucleotide is from 90% to 99.5% by weight pure. The polynucleotide of the present invention is preferably substantially pure.

Coding sequence: The term "coding sequence" means a polynucleotide that directly specifies an amino acid sequence of a polypeptide. The coding sequence is generally delimited by an open reading frame usually starting with the ATG start codon or alternative start codons such as GTG and TTG, and terminated with stop codons such as TAA, TAG and TGA. The coding sequence may be a DNA, cDNA, synthetic or recombinant polynucleotide.

cDNA: The term "cDNA" means a DNA molecule capable of being prepared by reverse transcription from a mature, spliced mRNA molecule derived from an eukaryotic cell. The cDNA lacks an intron sequence that is normally present in the corresponding genomic DNA. The initial, primary RNA transcript is a precursor to mRNA that is processed through a series of steps, including splicing, and then appears as mature, spliced mRNA.

Nucleic acid construct: The term "nucleic acid construct" means a single-stranded or double-stranded nucleic acid molecule that is isolated from a naturally occurring gene, is modified to contain a segment of a nucleic acid in such a way that it otherwise does not exist, or is synthetic. The term nucleic acid construct is synonymous with the term "expression cassette" when the nucleic acid construct contains the control sequences required for the expression of a coding sequence of the present invention.

Control sequence: The term "control sequence" means all components necessary for the expression of a polynucleotide encoding a polypeptide of the present invention. Each of the control sequences may be native or foreign to the nucleotide sequence encoding the polypeptide, or each of the control sequences may be native or foreign to each other. These control sequences include, but are not limited to, a leader sequence, a polyadenylation sequence, a propeptide sequence, a promoter, a signal peptide sequence, and a transcription terminator. The control sequences at least include a promoter as well as a termination signal for transcription and translation. The control sequences can be provided with a linker for the purpose of introducing a specific restriction site that facilitates the linkage of the control sequence to a coding region of the polynucleotide encoding the polypeptide.

Operatively linked: The term "operatively linked" means a configuration in which a control sequence is located at a proper position relative to the coding sequence of a polynucleotide such that the control sequence directs the expression of the coding sequence.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule comprising a polynucleotide that encodes a polypeptide, and is operatively linked to an additional nucleotide provided for its expression.

Host cell: The term "host cell" means any cell type that is susceptible to the transformation, transfection, and transduction, etc. of the nucleic acid construct or expression vector comprising the polynucleotide of the present invention. The term "host cell" encompasses any progeny of the parental cell that differs from the parental cell due to mutations that occur during replication.

Variant: The term "variant" means a protein or polypeptide having 3-epimerase activity that contains alterations at one or more (several) positions, i.e. substitution, insertion and (or) deletion of one or more (several) amino acid residues. Substitution means the replacement of an amino acid occupying a position with a different amino acid; deletion means removal of an amino acid occupying a position; and insertion means addition of 1-3 amino acids adjacent to an amino acid occupying a position.

DETAILED DESCRIPTION

The present inventors studied the characteristics of epimerase polypeptide derived from *Thermogemmatispora carboxidivorans*, and found that in the experiments of conversion of fructose into D-allulose and sorbose into D-tagatose, the polypeptide has the function of converting fructose or sorbose into D-allulose or D-tagatose by epimerizing the fructose or sorbose at the C-3 position. The polypeptide is obtained through a process comprising synthesizing an epimerase coding gene derived from *Thermogemmatispora carboxidivorans*, culturing a microorganism containing the gene expression vector and overexpressing the polypeptide. After experimenting, the peptide was found to have good allulose-3-epimerase and tagatose-3-epimerase activity and excellent thermal stability. Accordingly, the present invention provides a polypeptide having allulose-3-epimerase and tagatose-3-epimerase activity, and a method for producing D-allulose or D-tagatose by using the polypeptide having allulose-3-epimerase and tagatose-3-epimerase activity.

In order to determine the characteristics of the epimerase polypeptide, in the present invention, the gene encoding a polypeptide designated as epimerase derived from the *Thermogemmatispora carboxidivorans* is obtained by gene synthesis, and the gene encoding the polypeptide designated as epimerase is defined based only on the DNA base sequence, instead of the characterization results of the functions thereof. The obtained epimerase coding gene is then inserted into a suitable expression vector to produce a recombinant vector containing the epimerase coding gene, and the recombinant vector is transformed into a suitable microorganism. The transformed microorganism is cultured in a fermentation medium, and a polypeptide product of the epimerase coding gene is overexpressed in the microorganism. Then the polypeptide product of the epimerase coding gene is isolated and purified for later use. After experiment, the peptide is found to have allulose-3-epimerase and tagatose-3-epimerase activity, and can convert fructose into D-allulose and sorbose into D-tagatose.

The novel polypeptide having 3-epimerase activity produced by the method of the present invention may have an amino acid sequence which is not limited to the amino acid sequence as shown in SEQ ID No: 2, and includes amino acid sequences formed by the substitution, insertion, or deletion of one or more amino acid residues in the amino acid sequence of SEQ ID No: 2, as long as the protein or polypeptide with these amino acid modifications has allulose-3-epimerase and tagatose-3-epimerase activity and can convert fructose or sorbose to D-psicose or D-tagatose.

In the method of the present invention, the expression vector which can be used to produce a recombinant expression vector may be any expression vector conventionally used in genetic recombination techniques, and may be, for example, pET-22b(+). The microorganism capable of being transformed by the recombinant expression vector may be *E. coli* BL21 (DE3). However, the microorganism is not limited as long as it is any microorganism that can overexpress a desired gene after transformation with a recombinant expression vector containing the gene, and can produce an activity protein or polypeptide as a result of overexpression.

More specifically, the following process of culturing the transformed microorganism and inducing the overexpression of the protein or polypeptide of the present invention can be carried out according to an exemplary experimental scheme of the present invention as described below. The cryopreserved recombinant *E. coli* was inoculated into a 250 mL flask containing 50 mL of LB medium, and the strain was cultured in a shaker maintained at 37° C. until the absorbance at 600 nm reaches 2.0. The culture was added to a 7 L fermentor containing 5 L of fermentation medium containing 15 g/L peptone, 25 g/L yeast extract, 10 g/L sodium chloride, 2 g/L glucose, 3 g/L lactose and the mixture was cultured in the fermentor to induce the overexpression of the protein of the present invention. During the fermentation, the agitation rate was 500 rpm, the aeration rate was 1.0 vvm, and the culture temperature was 37° C., and the above culture conditions are favorable for the large-scale production of 3-epimerase.

For the purpose of purifying the protein produced by overexpression, the recombinant *E. coli* culture is centrifuged at 6,000×g and 4° C. for 30 minutes, and then washed twice with 0.85% NaCl. Subsequently, the cells were resuspended in 50 mM sodium phosphate buffer solution pH 8.0 (containing 300 mM NaCl), and the buffer solution containing the cells is placed in an ice bath for 30 minutes. The cells in the buffer solution are disrupted by a high-pressure homogenizer, and the disrupted cells are centrifuged at 13,000×g and 4° C. for 20 minutes, and removed. The supernatant is filtered through a membrane filter having a pore size of 0.45 µm and purified by fast protein chromatography under low temperature conditions. The filtrate containing the protein of the present invention is added to a HisTrap HP column equilibrated with 50 mM sodium phosphate buffer solution (pH 8.0) containing 300 mM NaCl and 10 mM imidazole. Subsequently, the HisTrap HP column is washed with the same sodium phosphate buffer solution, and the protein attached to the column is eluted over a concentration gradient of imidazole from 10 mM to 200 mM in the same sodium phosphate buffer solution at a flow rate of 1 mL/min. The eluate containing the protein of the present invention is added to a HiPrep 16/60 resin column equilibrated with a 50 mM sodium phosphate buffer solution pH 7.5 to remove the imidazole, and then the protein is eluted at a flow rate of 6 mL/min. The protein solution thus collected is added to a Sephacryl S-100 HR column equilibrated with a 50 mM sodium phosphate buffer solution pH 7.5 containing 0.15 M NaCl, and the protein is eluted at a flow rate of 6 mL/min. Finally the eluted protein is dialyzed in a 50 mM sodium phosphate buffer solution.

The protein of the present invention obtained as described above is 3-epimerase, and the molecular weight of the 3-epimerase as a monomer is 31,770 Da. The 3-epimerase is a metalloenzyme, and metal ions have obvious promotion on its activity.

According to another embodiment of the present invention, by means of the reaction catalyzed by 3-epimerase in the presence of a metal ion, the purpose of increasing the yield of D-allulose produced from fructose, and the purpose of increasing the yield of D-tagatose produced from sorbose can be achieved. The metal ion is selected from the group consisting of manganese, magnesium and cobalt in a concentration ranging from 0.5 to 5 mM, for example, 1 mM. When the concentration of the metal ion is less than 0.5 mM, the effect of increasing the conversion rate is not significant, and when the concentration of the metal ion is higher than 5 mM, there is no significant difference in the conversion rate.

The reaction between the 3-epimerase and fructose or sorbose can be carried out using a substrate (pH 6-8) having a concentration of 10-75% (w/w) at a temperature of 50-90° C. (i.e. fructose or sorbose solution). When the concentration of the substrate, fructose or sorbose, is in the range of 10-75% (w/w), the yield of D-allulose or D-tagatose is good, and the conversion rate is high; and the pH and temperature conditions in the above ranges are optimal pH and temperature ranges for the 3-epimerase activity.

The 3-epimerase has excellent thermal stability. After incubation at 60° C. for 12 hours, no decline in activity is detected. After incubation at 80° C. for 12 hours, above 80% of the activity remains, and after incubation at 90° C. for 8 hours, 50% of the activity still remains. The excellent thermal stability of the 3-epimerase is a good property for producing D-allulose and D-tagatose under high temperature conditions.

According to another embodiment of the present invention, the reaction for converting fructose to produce D-allulose and converting sorbose to produce D-tagatose by the 3-epimerase can be carried out by immobilizing the 3-epimerase on a carrier during the reaction, because the 3-epimerase immobilized on a carrier can retain enzyme activity for a long period of time and is convenient for repeated use. The carrier used in the embodiment of the present invention may be any carrier known for use in enzyme immobilization, and may be, for example, sodium alginate. Sodium alginate is a natural colloidal polysaccharide, which is abundant in algal cell walls and contains β-D-mannuronic acid and α-L-guluronic acid residues, where the β-D-mannuronic acid and the α-L-guluronic acid residues are randomly linked by a β-1,4 bond. Therefore, sodium alginate allows for stable immobilization of 3-epimerase and is favorable for obtaining of D-allulose or D-tagatose in high yield. To maximize the yield of D-allulose or D-tagatose, sodium alginate can be used to immobilize 3-epimerase at a concentration of 1.5-4% (w/v), for example at a concentration of 2.5% (w/v). When sodium alginate is used as a carrier for immobilizing 3-epimerase, a 3-epimerase solution is added to an aqueous sodium alginate solution which is once or twice the volume of the 3-epimerase solution. The mixture is then added dropwise to a 0.2 M calcium ion solution using a syringe pump and a vacuum pump to form 3-epimerase-sodium alginate composite spheres. These 3-epimerase-sodium alginate composite spheres can be directly used in the conversion of fructose to produce D-allulose and of sorbose to produce D-tagatose.

The 3-epimerase of the present invention has good activity for fructose and sorbose and also excellent thermal stability, both of which are excellent properties for producing D-allulose and D-tagatose under high temperature conditions. The method for producing D-allulose and D-tagatose according to the embodiments of the present invention is environmentally friendly because a microorganism-derived enzyme is used. Only a simple enzyme immobilization process is needed in the method, and the yield and production efficiency of D-allulose and D-tagatose are significantly improved, thus reducing the production costs and maximizing the production outcome.

The D-allulose and D-tagatose thus produced can be effectively used as an additive for foods or drugs.

Beneficial Effects

The 3-epimerase of the present invention has good activity for fructose and sorbose and also excellent thermal stability, both of which are excellent properties for producing D-allulose and D-tagatose under high temperature conditions. The method for producing D-allulose and D-tagatose according to the embodiments of the present invention is environmentally friendly because a microorganism-derived enzyme is used. Only a simple enzyme immobilization process is needed in the method, and the yield and production efficiency of D-allulose and D-tagatose are significantly improved, thus reducing the production costs and maximizing the production outcome.

The D-allulose and D-tagatose thus produced can be effectively used as an additive for foods or drugs.

BRIEF DESCRIPTION OF THE DRAWINGS

FIG. 2-1 is a curve showing the effect of pH on 3-epimerase activity in Example 5 of the present invention;

FIG. 2-2 is a curve showing the effect of temperature on 3-epimerase activity in Example 5 of the present invention;

DETAILED DESCRIPTION

Figure 1:
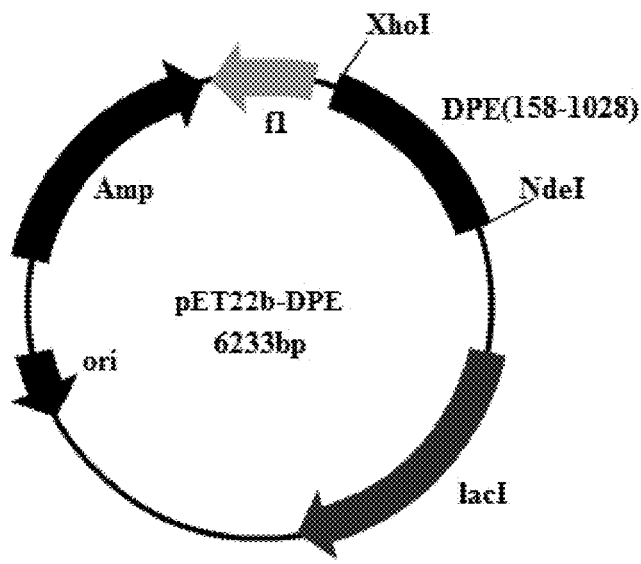
FIG. 1 is a flow chart of a process for producing 3-epimerase in Example 1 of the present invention.

Hereinafter, the present invention will be described in further detail with reference to specific examples. These Examples are for illustrative purposes only and are not intended to limit the scope of the present invention.

In the current experimental examples, the enzyme activity is measured using fructose and sorbose as substrates. In order to measure the enzyme activity, 3-epimerase is mixed with 50 mM sodium phosphate buffer solution (pH 7.5) containing 10% fructose or sorbose, reacted at 60° C. for 20 minutes, and then heated at 100° C. for 15 minutes to terminate the reaction. The sodium phosphate buffer solution containing fructose or sorbose is prepared by dissolving fructose or sorbose in a sodium phosphate buffer solution pH 7-8 to give a concentration of 60-70% (w/v). The sodium phosphate buffer solution containing fructose or sorbose is continuously added to a bioreactor maintained at 60° C. For the purpose of facilitating the comparison of enzyme activities, one unit of allulose-3-epimerase is defined as an amount of allulose-3-epimerase required to produce 1 mole of D-allulose per minute at pH 7.5 and 60° C.; and one unit of tagatose-3-epimerase is defined as an amount of tagatose-3-epimerase required to produce 1 mole of D-tagatose per minute at pH 7.5 and 60° C. The concentrations of fructose, D-allulose, sorbose, and D-tagatose are determined by high performance liquid chromatography with a BP-100 calcium ion hydrocarbon column and an RI detector. The column temperature is 80° C., and the mobile phase is ultrapure water with a flow rate of 0.5 mL/min.

Example 1: Production of 3-Epimerase

The 3-epimerase coding gene was obtained by synthesizing the gene encoding a polypeptide designated as epimerase derived from the *Thermogemmatispora carboxidivorans*, and the epimerase coding gene was defined based only on the sequence, instead of the characterization results of the functions thereof. The obtained epimerase coding gene was inserted into the expression vector pET-22b(+) by using restriction enzymes NdeI and XhoI to produce a recombinant expression vector pET-22b(+)/epimerase (see FIG. 1). This recombinant expression vector was transformed into *E. coli* BL21 (DE3) by a conventional transformation method.

The transformed recombinant *E. coli* BL21 (DE3) was stored in a freezer at an ultra-low temperature of −80° C.

Thereafter, the recombinant *E. coli* was inoculated into a 250 mL Erlenmeyer flask containing 50 mL of liquid LB medium, and cultured and activated in a shaker at 37° C. until the absorbance of the culture at a wavelength of 600 nm reached 2.0. This culture was added to a 7 L fermentor containing 5 L of fermentation medium, and subjected to fermentation culture to massively produce 3-epimerase. During the fermentation, the stirring rate was maintained at 500 rpm, the aeration rate was 1.0 vvm, and the culture temperature was 37° C.

Example 2: Purification of 3-Epimerase

To characterize the properties of 3-epimerase, 3-epimerase was purified by affinity chromatography (HisTrap HP column), HiPrep 16/60 column and Sephacryl S-100 HR column.

The molecular weight of the purified 3-epimerase was measured, and the 3-epimerase monomer was found to have a molecular weight of 31,770 Da. The amino acid sequence of the 3-epimerase was confirmed to be identical to the amino acid sequence deposited under NCBI Accession No. WP_052889376.

Example 3: Metal Dependence of 3-Epimerase

In Example 3, in order to investigate the effect of metal ions on the 3-epimerase, the effect on the activity of 3-epimerase was measured with fructose as a substrate in the presence of various metal ions. The measurement was carried out by treating 3-epimerase with EDTA, and then adding 1 mM of various metal ions shown in Table 1 below to the 3-epimerase solution. The reaction catalyzed by 3-epimerase was carried out in a 50 mM Tris buffer pH 7.5 at 60° C. for 20 minutes, where the Tris buffer contained 0.04 U/mL 3-epimerase and 10% (w/v) fructose. The reaction solution was further heated at 100° C. for 15 minutes to terminate the reaction, and then the activity of the 3-epimerase was measured.

The results show that the 3-epimerase is metal dependent. As shown in Table 1 below, magnesium, manganese and cobalt ions enhance the enzyme activity, while copper and zinc ions inhibit the enzyme activity.

TABLE 1

| Metal ion | Relative activity (%) |
|---|---|
| None | 100 |
| $Co^{2+}$ | 170 |
| $Ca^{2+}$ | 65 |
| $Mn^{2+}$ | 168 |
| $Mg^{2+}$ | 130 |
| $Zn^{2+}$ | 0 |
| $Cu^{2+}$ | 0 |
| $Na^+$ | 120 |
| $K^+$ | 113 |

Example 4: Specificity of 3-Epimerase for Substrate

The reaction catalyzed by 3-epimerase was carried out in a 50 mM sodium phosphate buffer solution pH 7.5 at 60° C. for 20 minutes, where the sodium phosphate buffer solution contained 0.04 U/ml 3-epimerase and 10 mM of various individual monosaccharides shown in Table 2 below. Each reaction solution was heated at 100° C. for 15 minutes to terminate the reaction, and then the enzyme activity of the 3-epimerase in each reaction solution was measured.

The results show that the 3-epimerase is active for D-fructose, D-allulose, D-sorbose, and D-tagatose. The 3-epimerase can be used to produce D-allulose as well as D-tagatose.

TABLE 2

| | Relative activity (%) |
|---|---|
| Fructose | 63.9 |
| D-allulose | 100 |
| Sorbose | 21 |
| D-tagatose | 40.7 |

Example 5: Effects of pH and Temperature on 3-Epimerase Activity

In Example 5, in order to study the effects of different pH and temperature on the 3-epimerase activity, the effect on the activity of 3-epimerase was measured with fructose as a substrate at different temperature and pH conditions, and the enzyme activities at different temperature and pH were compared. To investigate the effect of pH, the reaction catalyzed by 3-epimerase was carried out in a 50 mM sodium phosphate buffer solution having a pH ranging from 6.0-8.5, where the sodium phosphate buffer solution contained 0.04 U/mL 3-epimerase and 10% (w/v) fructose. Here, the respective reactions were carried out at 60° C. for 20 minutes in the absence of metal ions, and then the reaction was terminated by heating at 100° C. for 15 minutes, and the enzyme activity was measured. The result is shown in FIG. 2-1.

To investigate the effect of temperature, the reaction was carried out in a 50 mM sodium phosphate buffer solution (pH 7.5) at a temperature ranging from 40 to 90° C. for 20 minutes, where the sodium phosphate buffer solution contained 0.04 U/mL 3-epimerase and 10% (w/v) fructose. The reaction was terminated by heating at 100° C. for 15 minutes and the enzyme activity was measured. The results are shown in FIG. 2-2.

The result shows that the optimum pH and temperature for the 3-epimerase are 7.5 and 90° C., respectively.

Figures 1, 2:
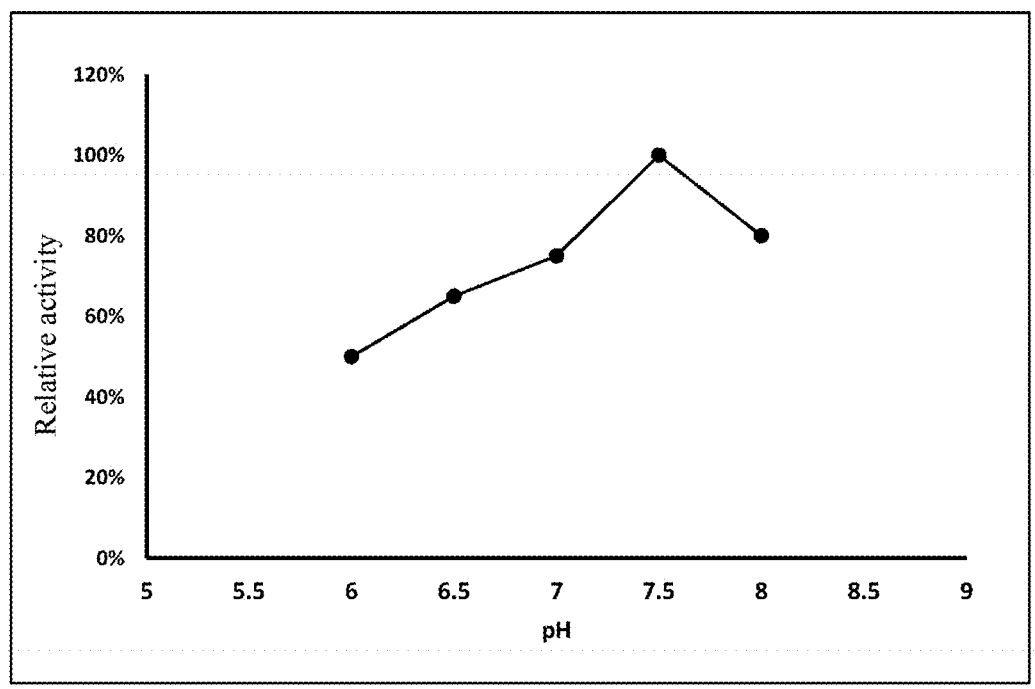
Figure 2:
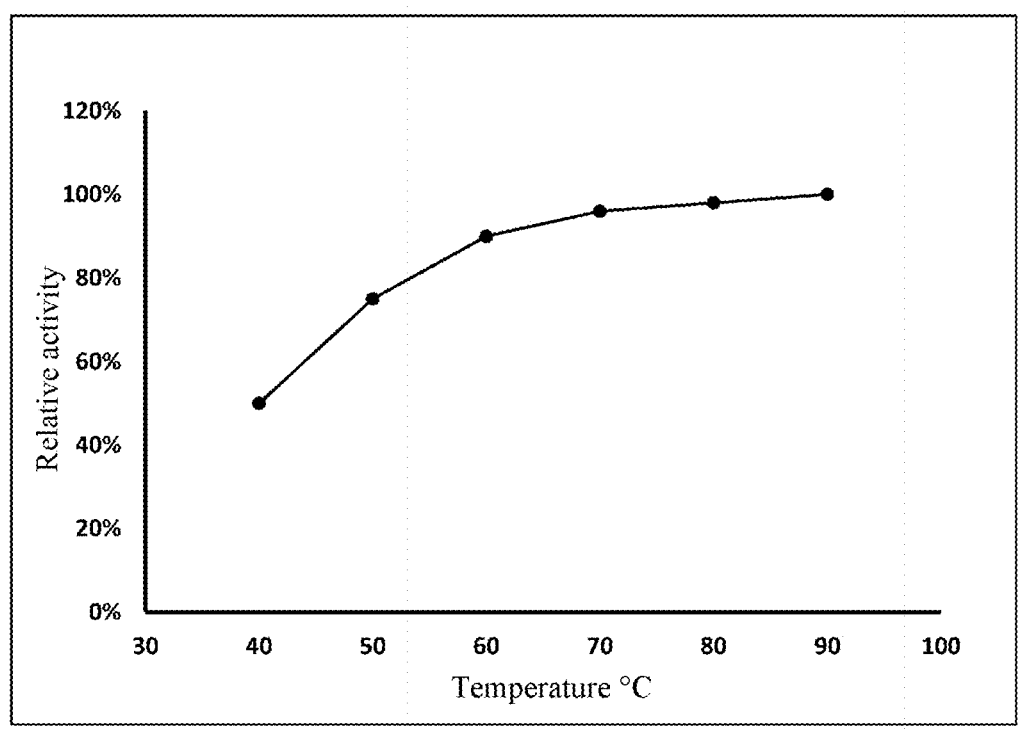

FIG. 2-1 is a curve showing the effect of pH on the 3-epimerase activity under the conditions in the example of the present invention.

FIG. 2-2 is a curve showing the effect of temperature on the 3-epimerase activity under the conditions in the example of the present invention.

Example 6: Thermal Stability of 3-Epimerase

Figure 3:
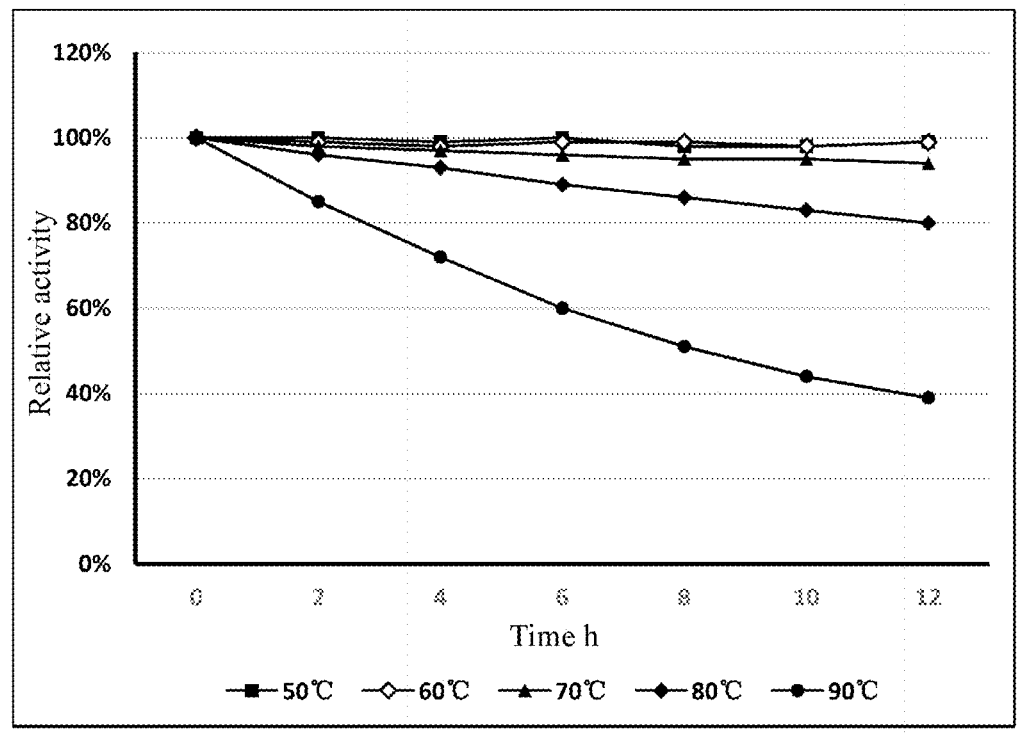
FIG. 3 shows the temperature-activity relationship in Example 6 of the present invention.

In Example 6, to study the thermal stability of 3-epimerase, the 3-epimerase was separately incubated at different temperature conditions, and samples were taken at different times to measure the remaining activity with fructose as a substrate. The measurement was performed by sampling every 1 hour after the 3-epimerase was maintained in a water bath at 50° C., 60° C., 70° C., 80° C. and 90° C. The reaction catalyzed by 3-epimerase was carried out in a 50 mM sodium phosphate buffer solution pH 7.5 at 60° C. for 20 minutes, where the sodium phosphate buffer solution contained 0.04 U/mL 3-epimerase and 10% (w/v) fructose. The reaction solution was further heated at 100° C. for 15 minutes to terminate the reaction, and then the activity of the 3-epimerase was measured. The results are shown in FIG. 3.

The result shows that 3-epimerase has excellent thermal stability. After incubation at 60° C. for 12 hours, no decline in activity is detected. After incubation at 80° C. for 12 hours, above 80% of the activity remains, and after incubation at 90° C. for 8 hours, 50% of the activity still remains.

Example 7: Conversion Rate of Fructose to D-Allulose by 3-Epimerase

Figure 4:
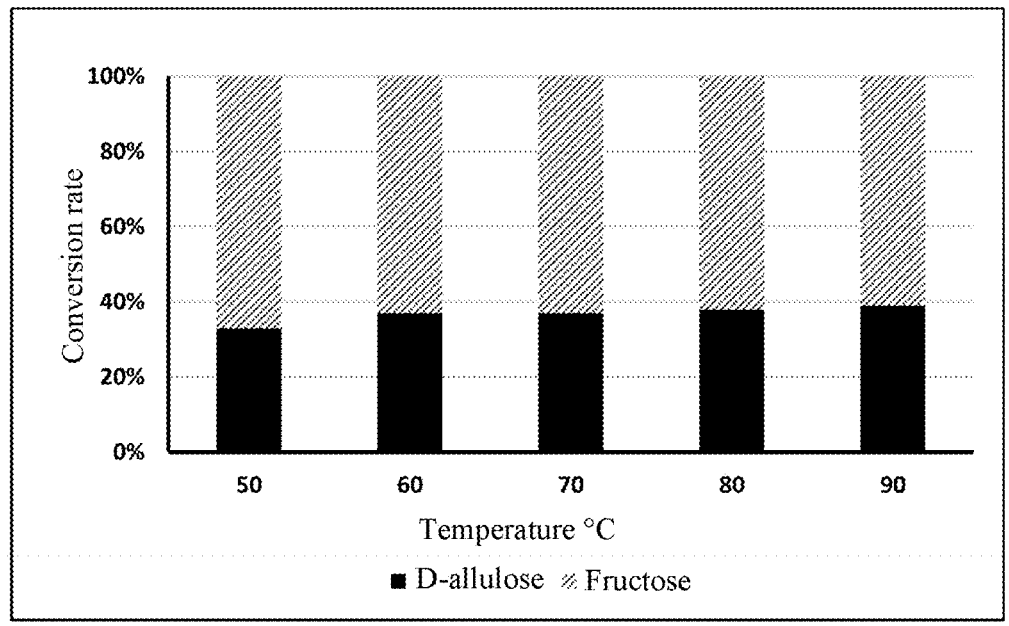
FIG. 4 is a schematic diagram showing the conversion rate of fructose to D-allulose by 3-epimerase in Example 7 of the present invention.

In Example 7, the reaction catalyzed by 3-epimerase was carried out in a 50 mM sodium phosphate buffer solution (pH 7.5) at a temperature ranging from 40 to 90° C. for 12 hours to allow the reaction to proceed sufficiently, where the sodium phosphate buffer solution contained 0.04 U/mL 3-epimerase, 1 mM cobalt ion, and 10% (w/v) fructose. The reaction was then terminated by heating at 100° C. for 15 minutes and the contents of fructose and D-allulose in the sample were measured. The results are shown in FIG. 4.

The result shows that after 12 hours, the conversion rate of fructose to D-allulose by 3-epimerase is the highest at 90° C. and is 39%, and is the lowest at 50° C. and is 22%; and the conversion at 60° C. is 37%.

Example 8: Production of D-Allulose by Using 3-Epimerase

To produce a high concentration of D-allulose, the reaction was carried out in a 50 mM sodium phosphate buffer solution (pH 7.5) at 60° C., where the sodium phosphate buffer solution contained 10 U/mL 3-epimerase, 1 mM cobalt ions and 700 g/L fructose. Then, samples were taken at various reaction times, and the reaction was then terminated by heating at 100° C. for 15 minutes and the concentration of D-allulose in the sample was measured. The yields of D-allulose at various reaction times is shown in Table 3 below.

TABLE 3

| | D-allulose (g/L) |
|---|---|
| 1 | 98 |
| 2 | 154 |
| 3 | 182 |
| 4 | 210 |
| 6 | 259 |
| 8 | 257 |

The results show that after 6 hours of reaction, 259 g/L D-allulose was produced with a conversion rate of about 37%.

Example 9: Production of D-Allulose by Immobilizing the Enzyme

To study the efficiency of the method for producing D-allulose, the 3-epimerase was immobilized. The production capability of immobilized 3-epimerase was measured and compared with that of non-immobilized (free) 3-epimerase.

For the 3-epimerase immobilized on a carrier, a 3-epimerase-sodium alginate composite sphere was used, which was prepared as follows. A 3-epimerase solution was added to a 2.5% (w/v) sodium alginate solution, where the volume of the sodium alginate solution was 1.5 times the volume of the 3-epimerase solution, and then the mixture was added to a 0.2 M calcium ion solution by using a syringe pump and a vacuum pump.

This reaction was carried out as described in Example 7, except that immobilized 3-epimerase was used. The amount of 3-epimerase used in this reaction was 10 U/mL, and the productivity of D-allulose was measured. The results are shown in Table 4 below.

TABLE 4

| Reaction time (h) | D-allulose (g/L) |
|---|---|
| 1 | 89 |
| 2 | 141 |
| 3 | 165 |
| 4 | 190 |
| 6 | 231 |
| 8 | 258 |
| 10 | 260 |

The results show that after 8-h reaction in the presence of immobilized 3-epimerase, a maximum yield of 258 g/L was reached, the conversion rate was about 37%, and the reaction rate was slightly slower than that with free 3-epimerase. However, the immobilized 3-epimerase is more conducive to continuous production, to achieve high-efficiency production of D-allulose.

Example 10: Production Yield of D-Allulose in Bioreactor

The following reaction was carried out in a bioreactor to test the production capability of immobilized 3-epimerase obtained in Example 9.

First, the immobilized 3-epimerase were prepared as described in Example 9. Fructose was added to the immobilized 3-epimerase, and the mixture was adjusted to a volume of 100 mL. Then, a bioreactor having a height of 100 cm and a diameter of 2.6 cm was filled with the mixture of immobilized 3-epimerase and fructose, and the reaction was carried out at a flow rate of 10 mL/h and 60° C.

The amount of 3-epimerase used was 500 U and the concentration of fructose used was restricted to 600 g/L, due to the precipitation of excess fructose during extended operation.

The results are shown in Table 5 below.

TABLE 5

| Time (day) | 1 | 2 | 3 | 5 | 10 | 15 | 20 | 25 | 30 |
|---|---|---|---|---|---|---|---|---|---|
| Productivity of D-allulose (g/L) | 189 | 222 | 219 | 221 | 220 | 222 | 219 | 221 | 220 |

The results are shown that the reaction between 3-epimerase and fructose is stable throughout the 30-day test period. The conversion of fructose to D-allulose is 37% and the concentration of D-allulose is 220 g/L. The yield can meet the needs of large-scale production of sugar.

Therefore, the present invention can provide a D-allulose production system utilizing a bioreactor capable of mass production on an industrial scale.

Example 11: Conversion Rate of Sorbose to D-Tagatose by 3-Epimerase

Figure 5:
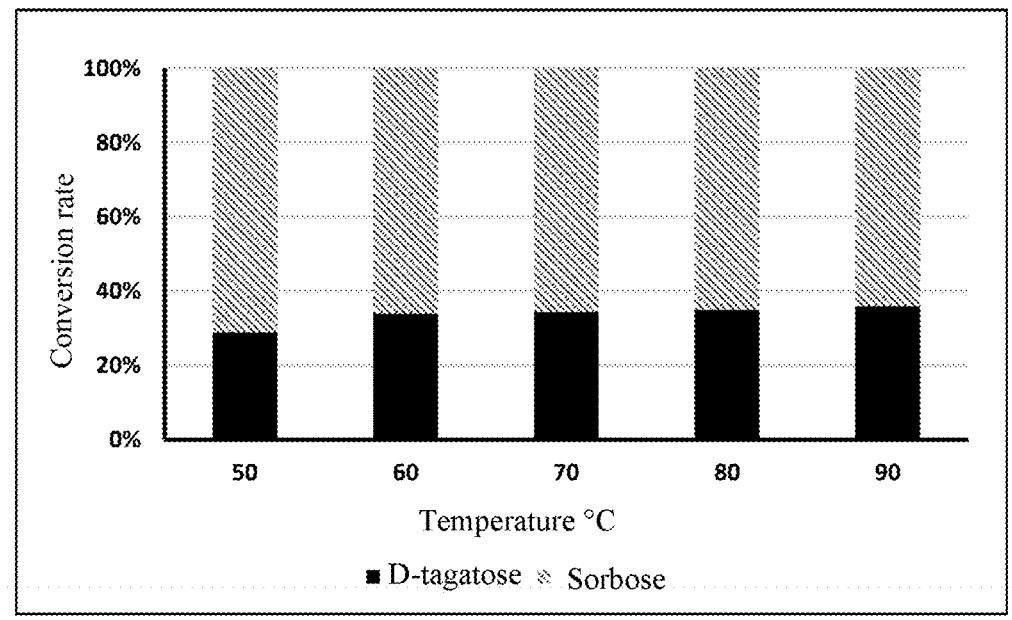
FIG. 5 is a schematic diagram showing the conversion rate of sorbose to D-tagatose by 3-epimerase in Example 11 of the present invention.

In Example 11, the reaction catalyzed by 3-epimerase was carried out in a 50 mM sodium phosphate buffer solution (pH 7.5) at a temperature ranging from 40 to 90° C. for 12 hours to allow the reaction to proceed sufficiently, where the sodium phosphate buffer solution contained 0.04 U/mL 3-epimerase, 1 mM cobalt ion, and 10% sorbose. The reaction was then terminated by heating at 100° C. for 15 minutes and the contents of sorbose and D-tagatose in the sample were measured. The results are shown in FIG. 5.

The result shows that after 12 hours, the conversion rate of sorbose to D-tagatose by 3-epimerase is the highest at 90° C. and is 36%, and is the lowest at 50° C. and is 29%; and the conversion at 60° C. is 34%.

Example 12: Production of D-Tagatose by Using 3-Epimerase

To produce a high concentration of D-tagatose, the reaction was carried out in a 50 mM sodium phosphate buffer solution (pH 7.5) at 60° C., where the sodium phosphate buffer solution contained 20 U/mL 3-epimerase, 1 mM cobalt ions and 500 g/L sorbose. Then, samples were taken at various reaction times, and the reaction was then terminated by heating at 100° C. for 15 minutes and the concentration of D-tagatose in the sample was measured. The yields of D-tagatose at various reaction times are shown in Table 6 below.

TABLE 6

| Reaction time (h) | D-tagatose (g/L) |
|---|---|
| 1 | 65 |
| 2 | 101 |
| 3 | 120 |
| 4 | 139 |
| 6 | 171 |
| 8 | 170 |

The results show that after 8 hours of reaction, 171 g/L D-tagatose is produced with a conversion rate of about 34%

Example 13: Production of D-Tagatose by Immobilizing the Enzyme

To study the efficiency of the method for producing D-tagatose, the 3-epimerase was immobilized. The production capability of immobilized 3-epimerase was measured and compared with that of non-immobilized (free) 3-epimerase.

For the 3-epimerase immobilized on a carrier, a 3-epimerase-sodium alginate composite sphere was used, which was prepared as follows. A 3-epimerase solution was added to a 2.5% (w/v) sodium alginate solution, where the volume of the sodium alginate solution was 1.5 times the volume of the 3-epimerase solution, and then the mixture was added to a 0.2 M calcium ion solution by using a syringe pump and a vacuum pump.

This reaction was carried out as described in Example 12, except that immobilized 3-epimerase was used. The amount of 3-epimerase used in this reaction was 20 U/mL, and the productivity of D-tagatose was measured. The results are shown in Table 7 below.

TABLE 7

| Reaction time (h) | D-tagatose (g/L) |
|---|---|
| 1 | 59 |
| 2 | 95 |

TABLE 7-continued

| Reaction time (h) | D-tagatose (g/L) |
|---|---|
| 3 | 108 |
| 4 | 125 |
| 6 | 153 |
| 8 | 170 |
| 10 | 171 |

The results show that after 10-h reaction in the presence of immobilized 3-epimerase, a maximum yield of 170 g/L is reached, the conversion rate is about 34%, and the reaction rate is slightly slower than that with free 3-epimerase. However, the immobilized 3-epimerase is more conducive to continuous production, to achieve high-efficiency production of D-tagatose.

Example 14: Production Yield of D-Tagatose in Bioreactor

The following reaction was carried out in a bioreactor to test the production capability of immobilized 3-epimerase obtained in Example 13.

First, the immobilized 3-epimerase were prepared as described in Example 13. Sorbose was added to the immobilized 3-epimerase, and the mixture was adjusted to a volume of 100 mL. Then, a bioreactor having a height of 100 cm and a diameter of 2.6 cm was filled with the mixture of immobilized 3-epimerase and sorbose, and the reaction was carried out at a flow rate of 10 mL/h and 60° C. The amount of 3-epimerase used was 400 U and the concentration of sorbose used was 400 g/L. The results are shown in Table 8 below.

TABLE 8

| Time (day) | 1 | 2 | 3 | 5 | 10 | 15 | 20 | 25 | 30 |
|---|---|---|---|---|---|---|---|---|---|
| Productivity of D-tagatose (g/L) | 115 | 135 | 136 | 136 | 137 | 135 | 137 | 135 | 136 |

The result shows that the reaction between 3-epimerase and sorbose was stable throughout the 30-day test period. The conversion of sorbose to D-tagatose was at 34% and the concentration of D-tagatose was 170 g/L. The yield can meet the needs of large-scale production of sugar.

Therefore, the present invention can provide a D-tagatose production system utilizing a bioreactor capable of mass production on an industrial scale.

What is claimed is:

1. A method of producing D-allulose, comprising contacting fructose, with an aqueous solution of a polypeptide or protein, said polypeptide or protein having the amino acid sequence identical to SEQ ID No: 2.

2. The method for producing D-allulose according to claim 1, wherein when the polypeptide or protein placed in contact with 10% (w/v) fructose at a temperature of 60° C. for 20 minutes at a pH of 7.5, the fructose is converted to the D-allulose.

3. The method for producing D-allulose according to claim 1, wherein the polypeptide or protein has enhanced enzyme activity in the presence of magnesium, manganese and cobalt ions whereas copper and zinc ions inhibit the enzyme activity.

4. The method for producing D-allulose according to claim 1, wherein when the polypeptide or protein are prepared in a phosphate buffer solution at 0.04 U/mL with 10% (w/v) fructose, an optimal pH is at 7.5 and an optimal temperature is at 90° C.

5. The method for producing D-allulose according to claim 1, wherein
the reaction is carried out in a 50 mM sodium phosphate buffer solution (pH 7.5) at 60° C.;
the sodium phosphate buffer solution contains 10 U/mL of the polypeptide or protein, 1 mM cobalt ions and 700 g/L fructose;
after 6 hours of reaction, the reaction is then terminated by heating at 100° C. for 15 minutes and D-allulose is produced with a conversion rate of about 37%.

6. The method for producing D-allulose according to claim 1, further comprising immobilizing the polypeptide or protein on a carrier, wherein a sodium alginate composite sphere is used as a carrier.

7. The method for producing D-allulose according to claim 6, further comprising
   carrying out a reaction between fructose and the polypeptide or protein in a bioreactor, said method comprising immobilizing the polypeptide or protein;
   adding fructose to the immobilized polypeptide or protein and obtaining a mixture, and adjusted the mixture volume to 100 mL;
   transferring the resulted mixture to the bioreactor having a height of 100 cm and a diameter of 2.6 cm; and
   carrying out the reaction at a flow rate of 10 mL/h and at 60° C.

8. The method for producing D-allulose according to claim 6, wherein a concentration of fructose used is restricted to 600 g/L, and reaction between the polypeptide or protein and fructose is stable throughout the 30-day period.

\* \* \* \* \*

SEQUENCE LISTING

```
<160> NUMBER OF SEQ ID NOS: 2

<210> SEQ ID NO 1
<211> LENGTH: 873
<212> TYPE: DNA
<213> ORGANISM: Thermogemmatispora carboxidivorans

<400> SEQUENCE: 1
atgaagcaga aaatcggtat tcacgcgttc gtgtgggttg gtggctggag cgaggaagag      60
tgccgtcaag cgctggagag cagccgtgcg agcggttacg acctgatcga gattccgctg     120
ctggaaccgg cggcgatcga tgtggcgctg acccgtagcc tgctggagaa gaccggtctg     180
gaagcgacct gcaccctggc gctgaccccg gaaaccgaca tcagcagcac cgatgaggcg     240
attgttgcgc gtggtgaacg tctgctgcac gacgcgctgg cggtggcgcg tgatctgggt     300
gcgagctacc tgggtggcgt tattttcggc gcgctgaccc gttatcgtga gccgctggcg     360
ccggcgggtc gtctgaacag catgcgtgtg ctggcgcgtc tggcggaaca ggcggcggtt     420
aacggtatgc aactgggcct ggaagtggtt aaccgttacg aaagcaactt tctgaacacc     480
gcggagcagg cgctgaacct gatcgaagag attggcgcgc cgaacctggt ggttcacctg     540
gacacctatc acatgaacat cgaagaggaa aacttcgtga agccggtggt tgcgtgcggt     600
aaacgtctgg gctacgtgca cgttggtgaa agccaccgtg gctatctggg taccggcacc     660
gtggattttc cgggtttctt tcgtgcgctg cgtcaggcgg ttatcaagg cccggttacc     720 ttcgagagct tagccgtgc gcaagaaatc gcgaacctga gcggtagcct ggcgatttgg     780
cgtcacacct ggaccgaccg tttcgatctg gcgcgtcagg cgcgtgcgtt tattgcggcg     840
ggtctggagg cgaccgacac ccaagaagat taa                                   873

<210> SEQ ID NO 2
<211> LENGTH: 290
<212> TYPE: PRT
<213> ORGANISM: Thermogemmatispora carboxidivorans

<400> SEQUENCE: 2
```

```
Met Lys Gln Lys Ile Gly Ile His Ala Phe Val Trp Val Gly Gly Trp
1               5                   10                  15

Ser Glu Glu Glu Cys Arg Gln Ala Leu Glu Ser Ser Arg Ala Ser Gly
            20                  25                  30

Tyr Asp Leu Ile Glu Ile Pro Leu Leu Glu Pro Ala Ala Ile Asp Val
            35                  40                  45

Ala Leu Thr Arg Ser Leu Leu Glu Lys Thr Gly Leu Glu Ala Thr Cys
        50                  55                  60

Thr Leu Ala Leu Thr Pro Glu Thr Asp Ile Ser Ser Thr Asp Glu Ala
65                  70                  75                  80

Ile Val Ala Arg Gly Glu Arg Leu Leu His Asp Ala Leu Ala Val Ala
                85                  90                  95

Arg Asp Leu Gly Ala Ser Tyr Leu Gly Gly Val Ile Phe Gly Ala Leu
            100                 105                 110

Thr Arg Tyr Arg Glu Pro Leu Ala Pro Ala Gly Arg Leu Asn Ser Met
            115                 120                 125

Arg Val Leu Ala Arg Leu Ala Glu Gln Ala Ala Val Asn Gly Met Gln
130                 135                 140

Leu Gly Leu Glu Val Val Asn Arg Tyr Glu Ser Asn Phe Leu Asn Thr
145                 150                 155                 160

Ala Glu Gln Ala Leu Asn Leu Ile Glu Glu Ile Gly Ala Pro Asn Leu
            165                 170                 175

Val Val His Leu Asp Thr Tyr His Met Asn Ile Glu Glu Glu Asn Phe
            180                 185                 190

Val Lys Pro Val Val Ala Cys Gly Lys Arg Leu Gly Tyr Val His Val
            195                 200                 205

Gly Glu Ser His Arg Gly Tyr Leu Gly Thr Gly Thr Val Asp Phe Pro
210                 215                 220

Gly Phe Phe Arg Ala Leu Arg Gln Ala Gly Tyr Gln Gly Pro Val Thr
225                 230                 235                 240

Phe Glu Ser Phe Ser Arg Ala Gln Glu Ile Ala Asn Leu Ser Gly Ser
            245                 250                 255

Leu Ala Ile Trp Arg His Thr Trp Thr Asp Arg Phe Asp Leu Ala Arg
            260                 265                 270

Gln Ala Arg Ala Phe Ile Ala Ala Gly Leu Glu Ala Thr Asp Thr Gln
            275                 280                 285

Glu Asp
290
```